Feb. 4, 1964 E. S. BOERNER Plant Pat. 2,352
CHRYSANTHEMUM PLANT
Filed Aug. 9, 1962 2 Sheets-Sheet 1
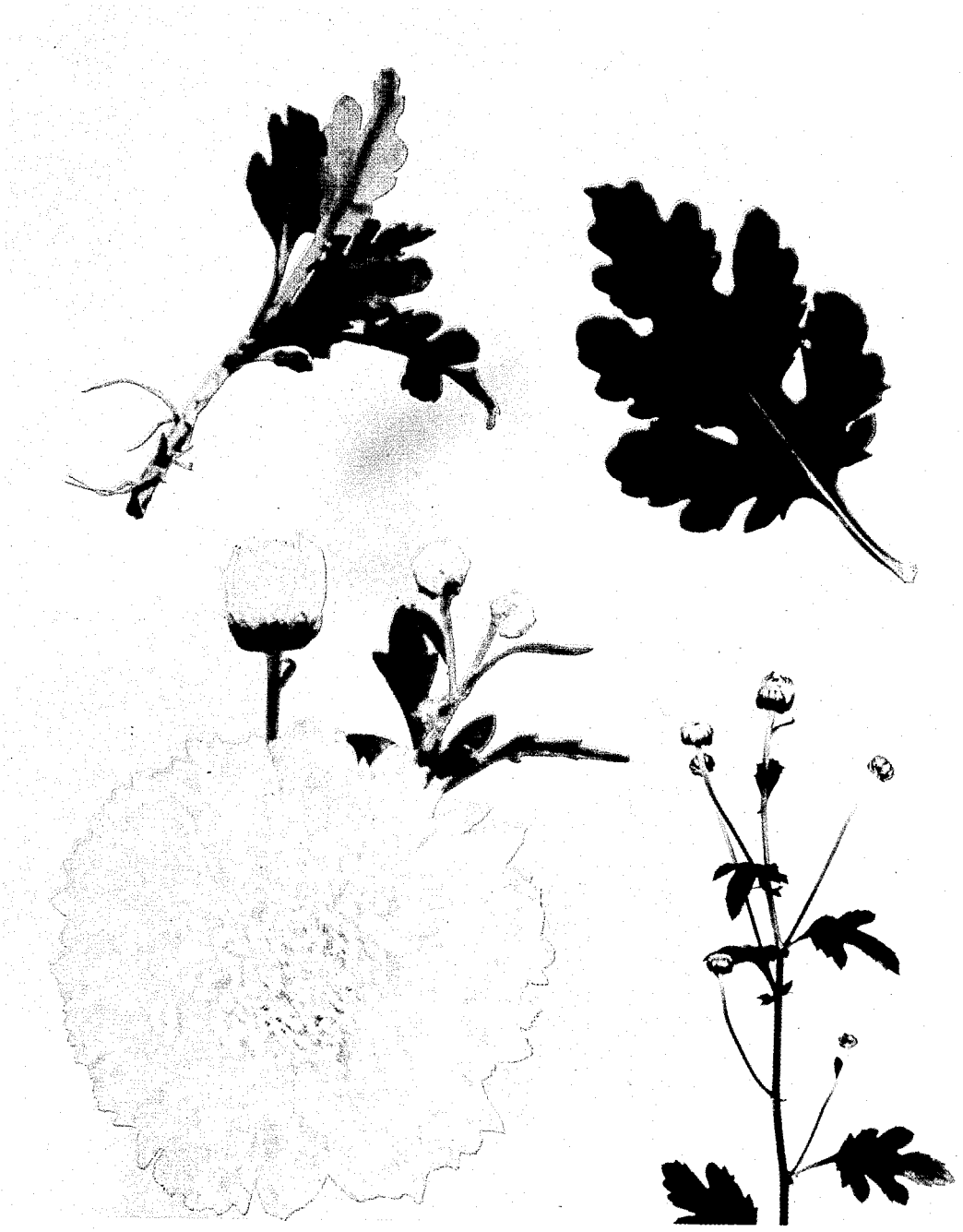
Inventor.
E. S. Boerner
By: Robb & Robb
Attorneys.

Feb. 4, 1964 E. S. BOERNER Plant Pat. 2,352
CHRYSANTHEMUM PLANT
Filed Aug. 9, 1962 2 Sheets-Sheet 2
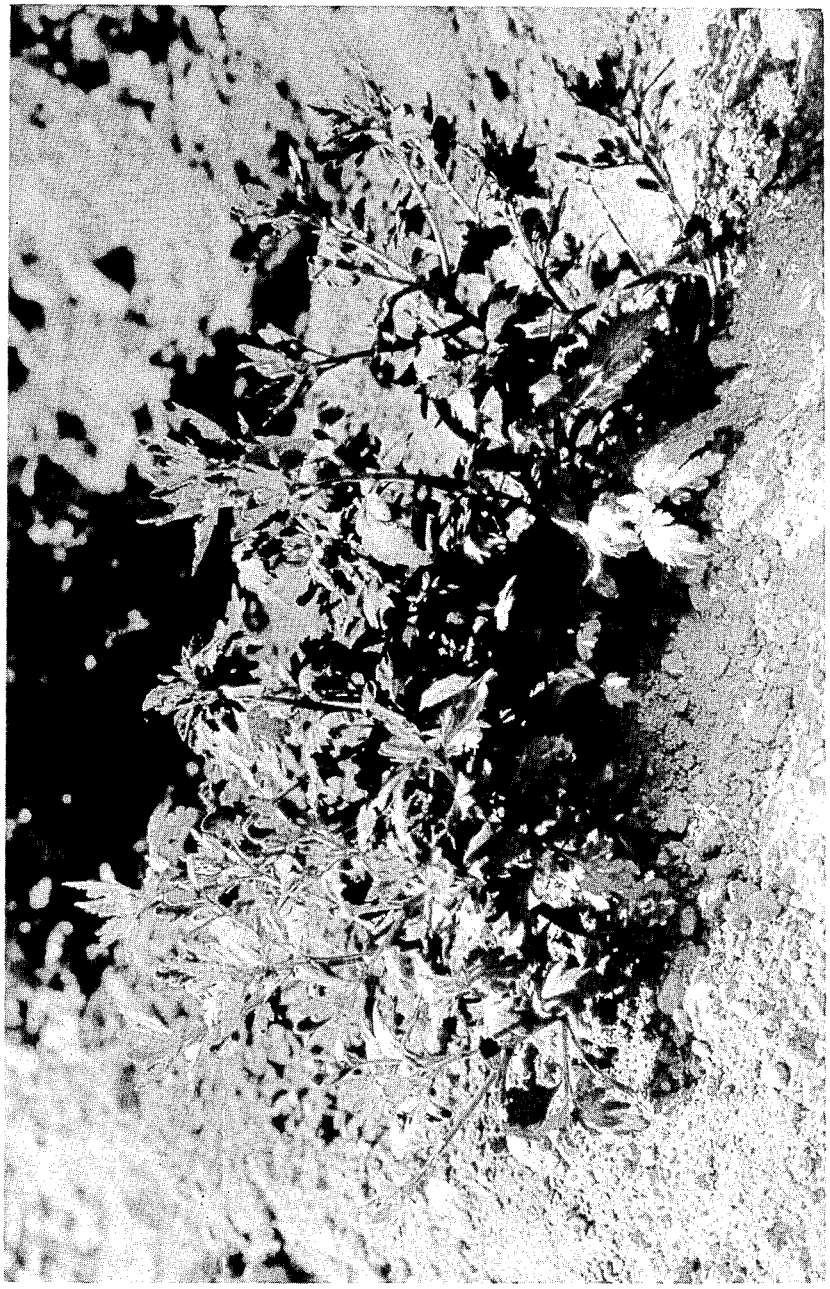
Inventor.
E. S. Boerner
By: Robb & Robb
Attorneys United States Patent Office Plant Pat. 2,352
Patented Feb. 4, 1964

2,352
CHRYSANTHEMUM PLANT

Eugene S. Boerner, Newark, N.Y., assignor to Jackson & Perkins Company, Newark, N.Y., a corporation of New York Filed Aug. 9, 1962, Ser. No. 216,006
1 Claim. (Cl. Plt.—78)

The present invention relates to a new and distinct variety of chrysanthemum plant of the decorative class, which was originated by me by crossing an unnamed and unpatented seedling of unidentified parentage with the variety known as "Swallow" (Plant Patent No. 1,106).

The primary objective of this breeding was to produce a new chrysanthemum variety in which there is combined the vigor and other growth habits of the unnamed seedling parent, along with the large size and decorative form of the flowers of the parent variety "Swallow." This objective was fully achieved, in addition to other desirable improvements, as evidenced by the following unique combination of characteristics which are outstanding in the new variety and which distinguish it from its parents, as well as from all other varieties of which I am aware:

(1) A vigorous, spreading and prostrate habit of growth;

(2) Large flower size and substantial thickness and decorative double form of the flowers; and (3) A distinctive and attractive general color tonality of the flowers corresponding to Empire Yellow, lightly overcast with Pale Lemon Yellow.

Asexual reproduction of the new variety by both top cuttings and underground runners, as performed outdoors at Newark, New York, shows that the foregoing characteristics and distinctions come true to form and are established and transmitted through succeeding propagations.

The accompanying drawings show typical specimens of the vegetative growth and flowers of my new chrysanthemum variety in different stages of development and as depicted in color as nearly true as it is reasonably possible to make the same in a color illustration of this character, as well as a typical specimen plant and a specimen flower stem which are depicted in black-and-white for the purpose of illustrating the form and the spreading and prostrate habit of growth of the plant.

The following is a detailed description of the new variety, with color terminology in accordance with Ridgway's Color Standards and Nomenclature, as based upon observations of specimens grown outdoors at Newark, New York, in the early afternoon during the latter part of the month of October:

Parentage: Seedling.
*Seed parent.*—An unnamed seedling of unidentified parentage.
*Pollen parent.*—"Swallow."

Classification: Decorative.
Growth: Prostrate; spreading; vigorous.
Cold resistance: Hardy in northern New York State.
Blooming period: From end of September until heavy frost.

*Flower*

Bud:
*Color.*—When sepals first divide—Picric Yellow, Plate 4. When petals begin to unfurl—Pale Lemon Yellow, Plate 4. When half-blown: inside—Lemon Yellow, Plate 4; outside—Picric Yellow, Plate 4.
*Peduncle.*—Color—Cress Green, Plate 31. Strength—strong.

Bloom:
*Size.*—Average 4 inches in diameter and 2 inches in thickness.
*Stem.*—Strong.
*Form.*—Decorative.
*Petalage.*—Double.
*Color.*—Center of flower—Lemon Chrome, Plate 4. Outer petals—Pale Lemon Yellow, Plate 4. Base of petals—Martius Yellow, Plate 4. Inside of petals—Empire Yellow, Plate 4, lightly overcast with Pale Lemon Yellow, Plate 4. Reverse of petals—Pale Greenish Yellow, Plate 5.
*Petals.*—Texture—crisp. Form—oval.
*Fragrance.*—Characteristic chrysanthemum.

*Plant*

Form: Prostrate; spreading.
Growth: Vigorous; free.
Foliage:
*Size.*—Normal.
*Quantity.*—Normal.
*Color.*—Upper side—Dark Cress Green, Plate 31. Reverse side—Light Elm Green, Plate 17.
*Texture.*—Leathery.

I claim:

A new and distinct variety of chrysanthemum plant of the decorative class, substantially as herein shown and described, characterized particularly as to novelty by the unique combination of a vigorous, spreading and prostrate habit of growth, large size and substantial thickness of the flowers, a decorative and double form of the flowers, and a distinctive and attractive general color tonality of the flowers corresponding to Empire Yellow, lightly overcast with Pale Lemon Yellow.

No references cited.